United States Patent [19]

Haneishi et al.

[11] Patent Number: 4,897,104
[45] Date of Patent: Jan. 30, 1990

[54] ANHYDRIDE HERBICIDES

[75] Inventors: Tatsuo Haneishi; Mutsuo Nakajima, both of Tokyo; Kiyoshi Koi, Shiga; Kohei Furuya, Tokyo; Seigo Iwado, Tokyo; Sadao Sato, Tokyo, all of Japan

[73] Assignee: Sankyo Company Limited, Tokyo, Japan

[21] Appl. No.: 184,409

[22] Filed: Apr. 21, 1988

[30] Foreign Application Priority Data

Apr. 27, 1987 [JP] Japan .................................. 62-103976

[51] Int. Cl.$^4$ .................... A01N 43/08; C07D 307/93
[52] U.S. Cl. .......................................... 71/88; 71/113; 435/119; 435/911; 549/243; 562/508
[58] Field of Search ............................. 71/88; 549/243

[56] References Cited

PUBLICATIONS

Chem. Abstracts, vol. 90, 1979, 90:98500u, Bondarevskaya.
M. O. Moss et al, J. Chem. Soc. (C), 1971, 619–624.
G. Buchi et al, J. Amer. Chem. Soc. (1970), 92, 6638–6641.
Chem. Abstracts, vol. 90 (1979), 90:146715s, p. 138.
Chem. Abstracts, vol. 72 (1970), 109237v, p. 205.
A. H. S. Brown et al, "Paecilomyces", pp. 40–49, Transactions British Mycological Society, vol. 40 (1957).

*Primary Examiner*—Richard L. Raymond
*Attorney, Agent, or Firm*—Frishauf, Holtz, Goodman & Woodward

[57] ABSTRACT

A novel compound named "cornexistin" has the formula (I):

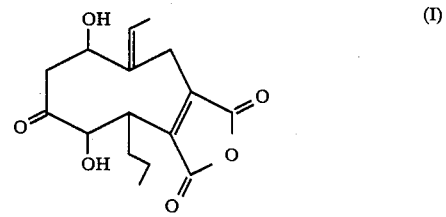

and it and the corresponding ring-opened diacid and salts thereof have herbicidal and growth regulating effects. Cornexistin can be prepared by cultivation of a microorganism of the genus Paecilomyces, e.g. *Paecilomyces variotii* Bainier SANK 21086.

2 Claims, No Drawings

ANHYDRIDE HERBICIDES

BACKGROUND TO THE INVENTION

The present invention relates to a novel composition of matter comprising a herbicide which may be produced by fermentation. It also relates to the method for its production and to the novel microorganism used in its production.

The closest prior art of which we are aware is the herbicidal compound known as Rubratoxin B [M. O. Moss et al., J. Chem Soc. (C), 1971, 619; and G. Büchi et al., J. Amer. Chem. Soc., (1970), 92, 6638], which may be represented by the formula (A):

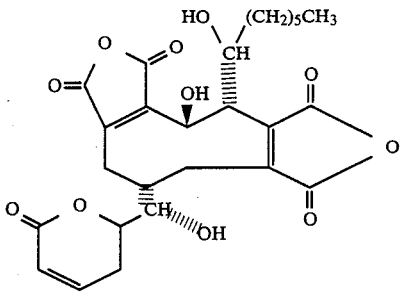

This is believed to have a herbicidal activity similar to that of the compounds of the present invention [F. G. Bondarevskaya et al., Fitotoksich. Svoistva Poshv. Mikroorganizmov., 1978, 205–12].

In accordance with the present invention, we have now discovered a novel compound which has a herbicidal activity significantly better than that of Rubratoxin B.

BRIEF SUMMARY OF INVENTION

The new compound of the present invention has now been named "Cornexistin" (although it was originally named "antlercidin") and may be represented by the formula (I):

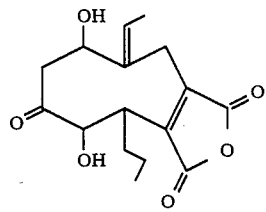

This compound is a cyclised internal anhydride, and can, in appropriate conditions, form the free dibasic acid, which may be represented by the formula (II):

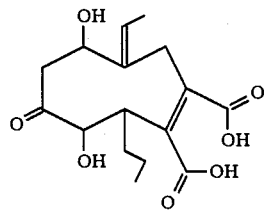

and this can form salts, the agriculturally acceptable ones of which also form part of the present invention.

The invention also provides an agrochemical composition for herbicidal use comprising an effective amount of cornexistin or said compound of formula (II) or a salt thereof as the active ingredient.

The invention still further provides a process for preparing cornexistin by cultivating a cornexistin-producing microorganism of the genus Paecilomyces, and separating cornexistin from the cultured broth.

The invention still further provides a process for preparing a compound of formula (II), as defined above, which process comprises treating cornexistin with water at a pH of above about 4.1.

The invention still further provides a process for preparing a salt of a compound of formula (II), as defined above, which process comprises treating cornexistin with an aqueous alkali at a pH of above about 4.1 and separating the salt from the aqueous medium.

DETAILED DESCRIPTION OF INVENTION

The new compound, cornexistin, of the present invention has the structure shown above by formula (I), and is believed to exist, when produced by fermentation, in the form of the isomer indicated by formula (Ia):

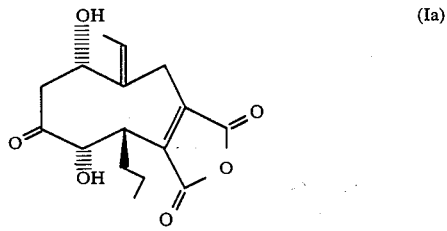

or its mirror image, although this has not been finally confirmed.

Cornexistin is scarcely soluble in water. However, on treatment with water, preferably water of a pH value higher than 4.1, and more preferably higher than 7, it can easily be converted into the acidic substance represented by the formula (II), shown above, which is water soluble, and which can form mono- or di- basic salts, depending on pH. The resulting acidic substance can be extracted with a water-immiscible organic solvent, such as ethyl acetate, at an acid pH, e.g. a pH value of 3 to 4. In that case, it reverts to cornexistin, represented by the original structural formula (I).

Cornexistin has the physicochemical properties shown below:

(1) Appearance: Fat-soluble, colorless needles;
(2) Melting point: 100°–103° C.;
(3) Specific rotation: $[\alpha]_D^{23}$ +168.3° (C=1.0, CHCl$_3$);
(4) Molecular formula: $C_{16}H_{20}O_6$;
(5) Molecular weight: 308;
(6) Ultraviolet absorption spectrum, $\lambda_{max}$ nm ($E_1$ cm$^1$%):
   The ultraviolet absorption spectrum determined in methanol shows a maximum absorption at 238 nm (131);
(7) Infrared Absorption Spectrum, $\nu_{max}$ (KBr) cm$^{-1}$: 3400, 3300, 2900, 1850, 1820, 1760, 1710, 1640, 1440, 1300, 1260, 1220, 1160, 1060, 1000, 920, 800, 760;
(8) $^1$H Nuclear Magnetic Resonance Spectrum, $\delta$ ppm:

The $^1$H-Nuclear Magnetic Resonance spectrum (270 MHz) determined in heavy chloroform, using TMS (tetramethylsilane) as the internal standard is as shown below:
0.93 (3H, triplet);
1.29 (2H, multiplet);
1.70 (3H, doublet);
1.90–2.1 (2H, multiplet);
2.57 (1H, doublet of doublets);
3.15 (1H, doublet);
3.4 (3H, multiplet)
4.07 (1H, doublet);
5.12 (1H, doublet of doublets);
5.85 (1H, doublet of doublets).

(9) Solubility: Soluble in ethanol, acetone, ethyl acetate, chloroform; practically insoluble in water; and insoluble in hexane;

(10) Color reactions: Positive to sulfuric acid and potassium permanganate;

(11) Thin layer chromatography: Rf=0.43;
Adsorbent: silica gel plate No. 5715 (Product of Merck & Co. Inc.); developing solvent: benzene: methanol: acetic acid (8:1:1 by volume);

(12) Biological activity
Cornexistin has germination inhibitory activity on the seeds of higher plants, herbicidal activity and a plant growth regulating effect.

Cornexistin is produced by the cultivation of a microorganism of the genus Paecilomyces, and preferably a microorganism of the species *Paecilomyces variotii* and more preferably the newly isolated strain herein referred to as *Paecilomyces variotii* Bainier SANK 21086, which also forms part of the present invention.

The newly discovered microorganism *Paecilomyces variotii* Bainier SANK 21086, is a fungus imperfectus, which was isolated from deer faeces. Its mycological properties are as follows.

It grows well on malt extract agar media, and the colony reaches a diameter of from 35 to 43 mm after culture at 24° C. for 7 days. The surface of the colony is at first colored Straw yellow 3B4, and is velvet-like. The center of the surface protrudes. As culture proceeds, the color becomes Greyish yellow 3C4, and the surface becomes slightly powdery. The reverse side is colored Greyish orange 5B3. [The color names used above are in accordance with "The Methuen Handbook of Colour", by A. Kornerup and J. H. Wanscher (1978), published by Eyre Methuen, London, England]. On Czapek agar media, it grows more slowly than on malt extract agar media, and the colony reaches a diameter of from 18 to 22 mm after culture at 24° C. for 7 days. At that time, the shape and color of the colony are similar to those on malt extract agar media. Although it grows very poorly at 37° C., conidium formation can be observed.

Under microscopic observation, the mycelia possess septa, are nearly colorless and have smooth surfaces, each 2 to 5 $\mu$m in diameter. Conidiophores are formed directly from aerial mycelia or basal mycelia, and each has a size of from 20 to 120 $\mu$m$\times$2.5 to 4.0 $\mu$m. Conidia are formed either from phialides on the conidiogenous structure in which divaricate branches are verticillated on the tips of conidiophores or from phialides formed on nearly unbranched hyphae. Phialides have a smooth surface and a size of from 10 to 40 $\mu$m$\times$2.5 to 4.0 $\mu$m each, and the tips appear as linear tubes. Conidia are pale brown in color, have a smooth surface, are long-chained and show a subglobose to ovoid shape having a size of from 3 to 5.5 $\mu$m$\times$2 to 4 $\mu$m each.

These properties of SANK 21086 were compared with those of known strains and good agreement was found with those of *Paecilomyces variotii* described by R. A. Samson ["Studies in Mycology" No. 6 (1974), published by C.B.S., P.14] and by A. H. S. Brown & G. Smith ["Transactions of the British Mycological Society", Vol. 40 (1957), p.40]. Therefore, SANK 21086 was identified as *Paecilomyces variotii* Bainier. The strain SANK 21086 was deposited on Apr. 24, 1987 with the Fermentation Research Institute, Agency of Industrial Science and Technology, Ministry of International Trade and Industry, Japan, under the conditions of the Budapest Treaty, with the deposit number FERM BP-1351.

It has been established that strain SANK 21086 produces cornexistin. However, as is well known, the properties of microorganisms of this type can vary considerably and such microorganisms can readily undergo mutation, both through natural causes and as the result of induction by artificial means. Accordingly, the process of the present invention embraces the use of any microorganism, especially any fungus imperfectus, which can be classified within the genus Paecilomyces and which shares with the new strain SANK 21086 the characteristic ability to produce cornexistin.

The cultivation of microorganisms of the genus Paecilomyces, and particularly strains of the species *Paecilomyces variotii*, in accordance with the present invention to produce cornexistin can be performed under conditions conventionally employed for the cultivation of fungi imperfecti, preferably in a liquid culture, and desirably with shaking or stirring and aeration. The nutrient medium used for the cultivation is completely conventional and contains such constituents as are commonly used in the cultivation of fungi imperfecti. Specifically, the medium should preferably contain an assimilable carbon source, suitable examples of which include glucose, maltose, sucrose, mannitol, molasses, glycerol, dextrin, starch (a particularly useful starch source for this microorganism, as for most fungi imperfecti, is fresh potato), soybean oil and cottonseed oil; an assimilable nitrogen source, suitable examples of which include soybean meal, peanut meal, cottonseed meal, Fermamine, fish meal, corn steep liquor, peptone, meat extract, yeast (e.g. pressed yeast), yeast extract, sodium nitrate, ammonium nitrate or ammonium sulfate; and one or more inorganic salts, such as sodium chloride, phosphates, calcium carbonate and, if required, trace metal salts. Where cultivation is effected in a liquid medium, it is generally desirable to incorporate an antifoaming agent (for example silicone oil, vegetable oil or a suitable surfactant) in the medium.

The cultivation is suitably performed in a medium at a pH which may range from weakly acidic to substantially neutral and at a temperature of from 20° to 30° C., more preferably about 24° C.

The production of cornexistin as cultivation proceeds may be monitored by a variety of conventional techniques for monitoring the production of biologically active substances by microbial culture and which require little or no elaboration here. A suitable technique is to assess the herbicidal activity of the cultured broth against a sensitive plant species, e.g. barnyard grass [*Echinochloa crus-galli* (L.) P. BEAUV.].

The amount of cornexistin produced normally reaches a maximum after cultivation has proceeded for between 150 to 200 hours and it is clearly desirable to separate the cornexistin from the culture medium no later than the time when this maximum has been reached. However, this period may vary, depending upon the cultivation conditions and techniques, and a shorter or longer period may be appropriate, depending upon the circumstances. The correct cultivation time may readily be assessed for every case by routine experiment, using suitable monitoring techniques, e.g. as described above.

Most of the cornexistin remains in the liquid portion of the cultured broth and it can thus be recovered by removing solid matter, including the mycelium, for example by filtration, preferably using a filter aid such as diatomaceous earth, or by centrifugation. It can then be recovered from the separated liquid portion by conventional techniques making use of its specific physicochemical properties and, if desired, then purified.

Cornexistin is preferably separated from other products in the liquid portion by means of an adsorbent, either by adsorbing the impurities or by adsorbing the cornexistin or by adsorbing both separately or together and then eluting the cornexistin. A wide range of adsorbents may be used; examples which we have found to be particularly satisfactory include: activated carbon; and resinous adsorbents such as Amberlite (registered trade mark) XAD-2, XAD-4 or XAD-7 (products of Rohm and Haas) and Diaion (registered trade mark) HP10, HP20, CHP20P or HP50 (products of Mitsubishi Chemical Industries Co., Ltd.). The impurities present in the liquid portion may be removed by passing the solution containing cornexistin through a layer or column of one or more of the aforementioned adsorbents or by adsorbing cornexistin on one or more of the adsorbents and then eluting the cornexistin with a suitable eluent. Suitable eluents include mixtures of methanol, acetone or butanol with water.

Alternatively, the cornexistin can be extracted directly from the filtrate of the cultured broth or an aqueous solution thereof under neutral to acidic conditions with a water-immiscible organic solvent, such as chloroform, ethyl acetate or butanol alone or as a mixture of any two or more thereof, and then purified.

The cornexistin thus obtained may be further purified by various means. Suitable methods include adsorption column chromatography using a carrier such as silica gel or Florisil, partition column chromatography using a cellulose product, such as Avicel (a registered trade mark for a product of Ashi Chemical Industry Co., Ltd.) or Sephadex LH-20 (a registered trade mark for a product of Pharmacia, Sweden) or by liquid chromatography using an ordinary or reverse phase column. The impurities present in the liquid portion containing the cornexistin may also beremoved by adsorbing them on various kinds of cation-exchange resins (strong or weak), such as Dowex 50W (a registered trade mark for a product of Dow Chemical Co., Ltd.) or Amberlite IRC-50 ( a registered trade mark for a product of Rohm and Haas), or on an anion-exchange resin (such as Dowex 1 or Diaion WA10). A single one or any combination of these purification techniques may be used in order to obtain pure cornexistin having the physicochemical properties described above.

When applied to plants, the compounds of the present invention are capable of inhibiting seed germination and regulating plant growth and have a herbicidal activity. Therefore, these compounds are believed to be potentially useful for plant growth regulation and weeding by preemergence soil treatment or foliar treatment of broadleaved or narrowleaved weeds and trees.

Cornexistin, the compound of this invention, shows a herbicidal effect. As is clearly demonstrated in Experiments 1, 2 and 3 hereafter, this compound has an excellent herbicidal effect on various kinds of weeds either by preemergence treatment or by postemergence treatment. In particular, it is useful when used as herbicide for foliar treatment. The compound of formula (II) and its salts (where the ring in the cornexistin molecule is open) also show a herbicidal effect, and are useful as herbicides.

The agrochemical composition of the present invention, whether for use as a herbicide or plant growth regulator, may comprise the cornexistin alone or the cornexistin in admixture with a carrier and/or adjuvant. The composition may be made into any form conventional in the agrochemical field, for example it may be formulated as a dust, a coarse dust, granules, microgranules, a wettable powder, a water-soluble powder or a liquid formulation. It is, of course, not necessary to use a completely pure form of cornexistin in the composition and, of course, purification can be suspended at any stage and the resulting crude substance may be used as the active ingredient of the composition.

The carriers used in such a composition may be a synthetic or natural, organic or inorganic substance and are mixed with the compound of the invention in order to make the storage, transportation and handling of the active ingredient easier or to assist translocation of the active ingredient into the plants. Carriers may be solid or liquid. Examples of solid carriers include such inorganic substances as: clay, talc, diatomite, kaolin, bentonite, calcium carbonate, gypsum, synthetic precipitated silica, attapulgite, zeolite or pumice; such synthetic and natural resins as cumarone resin, alkyd resins, polyvinyl chloride, ester gum or xanthan gum; such waxes as carnauba wax or paraffin wax; and other organic materials, such as nut shells (e.g. of walnuts or other nuts) or soybean powder. Examples of liquid carriers include: water; alcohols, such as methanol, ethanol, isopropanol or ethylene glycol; and hydrocarbons, such as xylene, methylnaphthalene and solvent naphtha.

Where the composition is to include a surfactant, this may be ionic or non-ionic and is used to assist dispersion, wetting or spreading of the composition. Examples of anionic surfactants include: salts of higher fatty acids, i.e. soaps, e.g. sodium oleate; salts, e.g. sodium and calcium salts, of sulfonic acids and the acids themselves, e.g. lignisulfonic acid, sodium dodecyl benzenesulfonate or sodium dialkyl sulfosuccinates; salts, e.g. sodium, ammonium and amine salts, of polyoxyethylene alkyl ether sulfates or of polyoxyethylene alkyl ether sulfates or the free acids; or salts of polyoxyethylene alkyl aryl ether phosphates or of polyoxyethylene alkyl phosphates. Examples of cationic surfactants include the higher aliphatic amines and ethylene oxide condensates with such amines, quaternary ammonium salts, e.g. chlorides, N-alkylamine acetates and N-alkylamine oxides. Amphoteric surfactants include betaines and amino acid-type surfactants. Examples of non-ionic surfactants include: glycerides and sucrose esters of fatty acids, ethylene oxide condensates with higher aliphatic alcohols, ethylene oxide condensates with alkylphenols or alkylnaphthols, amides or ethoxylated amides of higher fatty acids, higher fatty acid esters of sorbitan or of ethoxylated sorbitans, higher fatty acid esters of glycerol borates or of ethoxylated glycerol borates and copolymers of ethylene oxide with propylene oxide.

The agrochemical compositions of the present invention may, if desired, also contain other components, for example: protective colloids, such as gelatine, gum arabic, casein, polyvinyl alcohol or carboxymethyl cellulose; dispersing agents, such as sodium polyphosphate; inorganic dispersing agents, such as bentonite or veegum; stabilizers; binding agents; and anti-freezing agents. For wider applicability and labor saving, the composition of the invention can, if desired, be combined with one or more other agrochemicals, e.g. fungicides, insecticides, herbicides, plant growth regulators and fertilizers.

The preparation of cornexistin and its free acid form and salts thereof is further illustrated by the following non-limiting Examples. The preparation of formulations containing cornexistin is then illustrated by the subsequent Preparations, and the activity of cornexistin is illustrated by the subsequent Experiments.

EXAMPLE 1

One loopful growth of *Paecilomyces variotii* SANK 21086 was inoculated into a 500 ml baffled flask containing 80 ml of a medium having the composition shown below, and was cultured at 26° C. for 168 hour at 200 r.p.m. using a rotary shaker:

Medium components:

| Medium components | |
|---|---|
| Glycerol | 50 g |
| Fresh potato | 50 g |
| Yeast extract | 5 g |
| Malt extract | 5 g |
| Deionized water | 1 liter |

(pH = 6.0)

0.5 ml of the resulting seed culture was inoculated into each of twenty-five 500 ml baffled flasks, each containing 80 ml of the same culture medium as above, and the microorganism was cultured at 26° C. for 192 hours at 200 r.p.m. using a rotary shaker.

The resulting cultured broths, totalling 2 liters, were combined, and 200 g of Celite 545 (a trade mark for a product of Johns Manville Products Corp., U.S.A.) filter aid were added. The resulting mixture was then filtered, to give 1.7 liters of a filtrate (pH 6.0 ). This filtrate was passed through a column containing 300 ml of Diaion HP20 (Mitsubishi Chemical Industries Co.) to absorb the active substance. This active substance was then washed with 1 liter of deionized water, after which it was eluted with 1 liter of 80% v/v aqueous acetone, to give 1 liter of eluent. This 1 liter of eluent was condensed by evaporation under reduced pressure and then freeze dried, to afford 3 g of a crude powder containing the active compound, 2.7 g of this crude powder were dissolved in 400 ml of deionized water, and the pH of the solution was adjusted to a value of 2.5. It was then extracted twice, each time with 400 ml of ethyl acetate, to obtain 800 ml of an ethyl acetate solution containing cornexistin. The ethyl acetate solution was washed twice, each time with 300 ml of a 0.1M aqueous solution of dibasic sodium phosphate, and was then again washed twice, each time with 300 ml of a saturated aqueous solution of sodium chloride. The solution was then dried over anhydrous sodium sulfate, after which it was condensed by evaporation under reduced pressure, to give 650 mg of an oily substance containing cornexistin.

This oily substance was dissolved in a 1:1 by volume mixture of ethyl acetate and chloroform and was then subjected to chromatography through a column packed with 150 ml of Sephadex LH-20 [which had previously been equilibrated with a 1:1 by volume mixture of ethyl acetate and chloroform], where it was absorbed. It was then eluted with the same mixed solvent. The eluate was fractionated into 10 ml fractions, and the fractions containing cornexistin, Fractions Nos. 22 to 28, were collected and condensed by evaporation under reduced pressure, to give 100 mg of cornexistin having a purity of about 70%.

EXAMPLE 2

The same cultivation procedure as described in Example 1 was repeated, to give 1.8 liters of a culture filtrate. This filtrate was adjusted to a pH value of 2.5 and then extracted twice, each time with 1.5 liters of ethyl acetate, to obtain 3 liters of an ethyl acetate solution containing cornexistin. This solution was washed twice, each time with 1 liter of a 0.1M aqueous solution of dibasic sodium phosphate, and then again twice, each time with 1 liter of a saturated aqueous solution of sodium chloride. The solution was dried over anhydrous sodium sulfate, and was then condensed by evaporation under reduced pressure, to give 700 mg of an oily substance. This oily substance was passed through a column packed with 80 ml of Sephadex LH-20 (Pharmacia Co.) [which had previously been equilibrated with a 1:1 by volume mixture of ethyl acetate and chloroform], where it was absorbed and developed. It was then eluted with the same mixed solvent. The eluate was fractionated into 10 ml fractions and the fractions containing cornexistin, Fractions Nos. 13 to 18, were collected and condensed by evaporation under reduced pressure. The condensate was again subjected to chromatography through a similar Sephadex LH-20 column. After elution and fractionation, 290 mg of an oily substance were obtained.

The whole of this partly purified oily substance was then further purified by high performance liquid chromatography using a reverse phase column. More specifically, the sample was injected into a reverse phase column [(YMC;S-343 CI-15 ODS) Yamamura Chemical Industries Co., Ltd.] previously equilibrated with 40% v/v aqueous acetonitrile. By monitoring UV absorption at 240 nm, the sample was developed and eluted with the same mixed solvent at a flow rate of 5 ml/minute, and the fractions eluted between 30 and 39 minutes were collected. This procedure was repeated three times to obtain 185 mg of cornexistin having a purity of about 90%.

EXAMPLE 3

One loopful growth of *Paecilomyces variotii*, SANK 21086, was inoculated into a 500 ml baffled flask containing 80 ml of the same medium as described in Example 1, and was cultured at 26° C. for 144 hours at 200 r.p.m. using a rotary shaker. 75 ml of the resulting culture fluid were then inoculated into each of two 30 liter jar fermenters, each containing 15 liters of the same medium as described above, and the microorganism was cultured at 26° C. for 192 hours, whilst aerating at the rate of 15 liters/minute and stirring at 150 to 180 r.p.m. The 25 liters of culture fluid thus obtained were mixed with 1 kg of Celite (trade mark) 545 as a filter aid and were filtered. The resulting 19 liters of filtrate was adjusted to a pH value of 2.5, and extracted with 19 liters of ethyl acetate, and then with a further 9.5 liters of ethyl acetate, to obtain an ethyl acetate extract totalling about 28 liters. The extract was washed three times, each time with 5 liters of a 0.1M aqueous solution of dibasic sodium phosphate, and then again twice, each time with 5 liters of a saturated aqueous solution of sodium chloride. The washed extract was dried over anhydrous sodium sulfate, and then condensed by evaporation under reduced pressure, to give 2.02 g of an oily substance. The whole of this oily substance was dissolved in a 1:1 by volume mixture of ethyl acetate and chloroform and subjected to chromatography through a column packed with 500 ml of Sephadex LH-20 (which had previously been equilibrated with the same mixed solvent), where it was absorbed, developed and eluted with the same mixed solvent. The eluate was fractionated into 20 ml fractions, and the fractions containing cornexistin, Fractions Nos. 35 to 52, were collected. Condensation by evaporation under reduced pressure gave 7.56 g of an oily substance. The whole of this oily substance was dissolved in 10 of methylene chloride and was allowed to stand at room temperature, to afford 3.7 g of cornexistin as colorless needles.

EXAMPLE 4

Cornexistin was dissolved in 10% v/v aqueous ethanol and titrated with a 1N aqueous solution of sodium hydroxide. It showed 2 $pK_a$ values of 4.1 and 5.95, thus demonstrating that the anhydride form of cornexistin [formula (I)] had been converted to the ring opened free acid of formula (II).

EXAMPLE 5

Preparation of Mono- and Di- Sodium Salts of Cornexistin

Cornexistin, prepared as described in Examples 1 to 3, was suspended in water, and the pH was adjusted to a value of 6.1 (for the monosodium salt) or 7.95 (for the disodium salt) by the addition of a 1N aqueous solution of sodium hydroxide. The cornexistin dissolved, and then the resulting solution was partially evaporated, to remove the major part of the water. It was then lyophilized to remove the remainder of the water, and give either the monosodium salt or the disodium salt of cornexistin.

Monosodium Salt $[\alpha]_D^{23}$ +63.13° (C=1.15, water).
FAB Mass Spectrum: 349 (M+H)$^+$, (FAB is Fast Atom Bombardment).
Ultraviolet absorption spectrum (H$_2$O) $\lambda_{max}$ nm: 235 (shoulder).
Infrared Absorption Spectrum (KBr) $\nu_{max}$ cm$^{-1}$: 3400, 2960, 1705, 1564, 1450, 1440, 1050, 1010.
$^1$H Nuclear Magnetic Resonance spectrum (270 MHz, D$_2$O) $\delta$ ppm:
 0.68 (3H, triplet);
 1.05–1.21 (3H, multiplet);
 1.49 (3H, doublet);
 1.59 (1H, multiplet);
 2.62 (1H, doublet of doublets);
 2.75 (1H, triplet of doublets);
 2.85 (2H, doublet of doublets);
 3.22 (1H, doublet of doublets);
 4.00 (1H, doublet);
 4.90 (1H, doublet of doublets);
 5.46 (1H, doublet of doublets).

Disodium Salt $[\alpha]_D^{23}$ +61.15° (C=1.22, water).
FAB Mass Spectrum: 371 (M+H)$^+$.
Ultraviolet absorption spectrum (H$_2$O) $\lambda_{max}$ nm: 235 (shoulder).
Infrared Absorption Spectrum (KBr) $\nu_{max}$ cm$^{-1}$: 3400, 2960, 1705, 1562, 1450, 1400, 1050, 1010.
$^1$H Nuclear Magnetic Resonance spectrum (270 MHz, D$_2$O) $\delta$ ppm:
 0.68 (3H, triplet);
 1.05–1.22 (3H, multiplet);
 1.49 (3H, doublet);
 1.58 (1H, multiplet);
 2.62 (1H, doublet of doublets);
 2.72 (1H, triplet of doublets);
 2.85 (2H, doublet of doublets);
 3.22 (1H, doublet of doublets);
 4.01 (1H, doublet);
 4.89 (1H, doublet of doublets);
 5.44 (1H, doublet of doublets).

The preparation of agrochemical formulations is illustrated by the following Preparations. Hereinafter, all references to "parts" means parts by weight.

PREPARATION 1

Granules

One part of cornexistin was dissolved in 10 parts of methanol, and the solution was absorbed on 99 parts of pumice grains, which had previously been sieved through a 10 to 48 mesh sieve (Tyler standard mesh). The mixture was dried by volatilization of the methanol, to give granules containing 1% w/w cornexistin.

PREPARATION 2

Wettable Powder

Ten parts of cornexistin, 3 parts of sodium dodecylbenzenesulfonate, 2 parts of polyvinyl alcohol, 20 parts of diatomite and 65 parts of clay were mixed and pulverized to obtain a wettable powder.

PREPARATION 3

Wettable Powder

Fifty parts of cornexistin, 2 parts of polyoxyethylene nonylphenyl ether, 10 parts of synthetic silica and 38 parts of ammonium sulfate were mixed and pulverized to obtain a wettable powder.

PREPARATION 4

Liquid Formulation

Ten parts of cornexistin and 2 parts of sodium laurylsulfate were mixed and dissolved in 88 parts of methanol to obtain a liquid formulation.

PREPARATION 5

Emulsifiable Concentrate

Ten parts of cornexistin were dissolved in 75 parts of xylene, and then 15 parts of Paracol KPS (Nippon Nyukazai Co., Ltd.) were added and the whole was mixed to obtain an emulsifiable concentrate.

The activity of the herbicidal compounds of this invention is illustrated by the following Experiments.

EXPERIMENT 1

Herbicidal Effect on Young Barnyard Grass

The bottom of a test tube (10 mm×100 mm) was covered with absorbent cotton to a height of about 5 mm. The cotton layer was then permeated with 1 ml of water. About ten grains of barnyard grass seed [*Echinochloa crus-galli* (L.) P. BEAUV.] were placed on the cotton layer, and allowed to grow to a height of about 80 mm in a greenhouse. Aqueous solutions of cornexistin of various concentrations were prepared by dilution of a 10% w/v ethanolic solution of cornexistin. Each of the aqueous solutions so prepared was mixed with a New Gramin spreader (Sankyo Co., Ltd.) in an amount of 0.01% by weight, and the resulting composition was sprayed onto the foliage. The treated weeds were allowed to stand for about 10 days in a greenhouse, and then the herbicidal effect of the compounds at the various concentrations were assessed. The minimum herbicidal concentration of cornexistin against barnyard grass was determined to be 50 µg/ml.

EXPERIMENT 2

Herbicidal Test by Foliar Treatment

Plastic pots each 7.5 cm long, 20 cm wide and 7 cm high were packed with soil, on which 8 kinds of plants including 4 kinds of gramineous weeds and 4 kinds of broadleaved weeds were seeded, and covered with soil each to a depth of about 1 cm. The pot was buried in vermiculite in a box, which was placed on a bench in a greenhouse. Supplying water indirectly through vermiculite, the weeds were allowed to grow for about 2 weeks. At the end of this time, 5 cc per pot of sample solutions of cornexistin or its sodium salt at various concentrations (previously prepared in the form of wettable powders as described in Preparation 2) was applied directly to the foliage of the weeds. All changes taking place after application of the herbicide were observed, and after 14 days the plants were examined adn the effects were judged. The results are shown in Tables 1 (cornexistin) and 2 (monosodium salt of cornexistin). The herbicidal effect is reported according to the following criteria:

The percentage area of foliage killed in the treated weeds to that of the untreated weeds:

|  | Rating |
|---|---|
| 0–10% | 0 |
| 11–30% | 1 |
| 31–50% | 2 |
| 51–70% | 3 |
| 71–90% | 4 |
| 91–100% | 5 |

TABLE 1

Effect of cornexistin by foliar treatment

|  | Weeds | Concentration (active ingredient ppm) 500 | 100 |
|---|---|---|---|
| Gramineous weed | Giant foxtail (*Setaria faberi* HERRM) | 5 | 5 |
|  | Large crabgrass (*Digitaria sanguinalis* (L.) SCOP.) | 5 | 4 |
|  | Johnson grass (*Sorghum halepense* (L.) PERS.) | 5 | 5 |
|  | Barnyard grass | 5 | 2 |
| Broad leaf weed | Tall morning glory (*Ipomoea purpurea* (L.) ROTH) | 5 | 4 |
|  | Black nightshade (*Solanum nigrum* L.) | 5 | 5 |
|  | Velvetleaf (*Abutilon theophrasti* MEDIK) | 5 | 5 |
|  | Common cocklebur (*Xanthium pennsylvanicum* MALLR) | 5 | 5 |

TABLE 2

Effect of cornexistin monosodium salt by foliar treatment

|  | Weeds | Concentration (active ingredient ppm) 500 | 100 |
|---|---|---|---|
| Gramineous weed | Giant foxtail | 5 | 4 |
|  | large crabgrass | 4 | 2 |
|  | Johnson grass | 4 | 3 |
|  | Barnyard grass | 4 | 2 |
| Broad leaf weed | Tall morning glory | 5 | 3 |
|  | Black nightshade | 5 | 5 |
|  | Velvetleaf | 5 | 5 |
|  | Common cocklebur | 5 | 5 |

For comparison, under the same conditions, the activities of Rubratoxin B against gramineous weeds and against broadleaved weeds were 0 and 1.5, respectively.

EXPERIMENT 3

Preemergence Soil Treatment Test

Plastic pots each 7.5 cm long, 20 cm wide and 7 cm high were packed with soil, on which 8 kinds of plants including 4 kinds of gramineous weeds and 4 kinds of broadleaved weeds were seeded, and covered with soil each to a depth of about 1 cm. The pots were then placed on vermiculite in a box which was placed on a bench in a greenhouse. The surface of the soil in each pot was treated with 15 cc per pot of one of the sample solutions of cornexistin of various concentrations prepared as described in Experiment 2, one day after sowing. After 20 days, the plants were examined and the effects were judged. Table 3 shows the results. The herbicidal effect was assessed according to the following criteria:

The percentage growth inhibition of the treated weeds to that of the untreated weeds:

|  | Rating |
|---|---|
| 0–10% | 0 |
| 11–30% | 1 |
| 31–50% | 2 |
| 51–70% | 3 |
| 71–90% | 4 |
| 91–100% | 5 |

TABLE 3

Effect of cornexistin by preemergence soil treatment

| | | Dosage (active ingredient kg/ha) | |
|---|---|---|---|
| | Weeds | 4 | 2 |
| Gramineous weed | Giant foxtail | 5 | 4 |
| | Large crabgrass | 4 | 3 |
| | Johnson grass | 4 | 2 |
| | Barnyard grass | 4 | 3 |
| Broad leaf weed | Tall morning glory | 4 | 3 |
| | Black nightshade | 3 | 3 |
| | Velvetleaf | 5 | 5 |
| | Common cocklebur | 3 | 2 |

We claim:

1. A compound of formula (I):

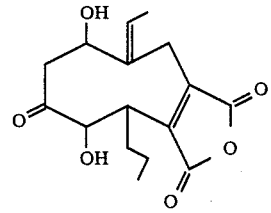

2. An agrochemical composition for herbicidal use comprising (i) at least one of a carrier and an adjuvant and (ii) an effective amount of a compound of formula (I):

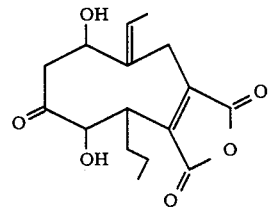

* * * * *